(12) United States Patent
Suzuki et al.

(10) Patent No.: US 6,483,589 B1
(45) Date of Patent: Nov. 19, 2002

(54) LASER SPECTROSCOPY SYSTEM

(75) Inventors: Katsumasa Suzuki, Tokyo (JP);
Hiroshi Masusaki, Tokyo (JP);
Takayuki Satoh, Tokyo (JP)

(73) Assignee: Nippon Sanso Corporation, Tokyo (JP)

( * ) Notice: Subject to any disclaimer, the term of this patent is extended or adjusted under 35 U.S.C. 154(b) by 355 days.

(21) Appl. No.: 09/611,260

(22) Filed: Jul. 6, 2000

(30) Foreign Application Priority Data

Jul. 12, 1999 (JP) .............................. 11-197984

(51) Int. Cl.[7] .............................................. G01N 21/31
(52) U.S. Cl. ....................................... 356/437; 356/436
(58) Field of Search ................................. 356/437, 436, 356/435, 434, 433, 432

(56) References Cited

U.S. PATENT DOCUMENTS 5,705,816 A * 1/1998 Ronge et al. ................ 356/437

* cited by examiner

*Primary Examiner*—Hung Xuan Dang
(74) *Attorney, Agent, or Firm*—Merchant & Gould P.C.

(57) ABSTRACT

In order to provide a laser spectroscopy system of simple construction and free of the effect of the fringe noise and to provide a laser spectroscopy system in which a reference cell is efficiently installed with minimum cost and space, there is disclosed a laser spectroscopy system comprising: a tunable laser diode source for generating a laser beam used for spectroscopic analysis; a sample cell where a sample gas is introduced; a first photo detector for measuring an intensity of a laser beam transmitted through the sample cell and having a beam receiving face; a beam splitter for splitting a portion of the laser beam from the laser source; and a second photo detector for measuring an intensity of a splitted laser beam from the beam splitter and having a beam receiving face, wherein the at least one of beam receiving faces is tilted to be at a predetermined angle from an axis of laser beam.

2 Claims, 7 Drawing Sheets

LASER SPECTROSCOPY SYSTEM

FIELD OF THE INVENTION

The present invention relates to a laser spectroscopy system, particularly to a spectroscopy system using a tunable laser diode as the optical source for analyzing a very small amount of ingredients included in a gas through infrared spectroscopy.

BACKGROUND OF THE INVENTION

Conventionally, an infrared spectroscopy system is widely used as an analyzer for analyzing ingredients in the gaseous sample, for example analyzing impurities included in a gas sample. The conventional infrared spectroscopy is the technique to measure an absorption spectrum by transmitting an infrared beam into the sample gas and to analyze this absorption spectrum, so that it is possible to identify the molecules (impurities) to be measured in the sample gas from the wavelength of the absorbed beam in the absorption spectrum and to determine the amount of the molecules from the amount of absorbed beam in the absorption spectrum. Particularly, since it is known that the conventional spectroscopy which uses a near-infrared laser diode as the optical source has high sensitivity and precision, the conventional spectroscopy is used for determining the small amount of water molecules in the semiconductor material gases manufactured or used in the field of semiconductor industry and the related materials industry, or diagnosing diseases by analyzing the stable isotopes in the patients' exhalation.

FIG. 3 is a diagram which shows a general configuration of a conventional spectroscopy system using a laser diode as the optical source. The spectroscopy system shown in FIG. 3 includes an optical system which has a tunable laser diode source 10 for generating a laser beam for measurement, a sample cell 11 where a sample gas is introduced, the first photo detector 12 for measuring an intensity of a laser beam transmitted through the sample cell 11, two beam splitters 13 and 14 for splitting a portion of the laser beam from the laser source 10, the second photo detector 15 for measuring an intensity of a laser beam splitted (reflected) by the first beam splitter 13, a reference cell 16 where an object to be measured is introduced under depressurized condition, and the third photo detector 17 for measuring an intensity of a laser beam splitted (reflected) by the second beam splitter 14 and transmitted through the reference cell 16. Generally, this optical system is contained in a purge box 18. Further, the laser source 10 has driving means 10a and 10b for controlling driving current and operating temperature. The photo detectors 12, 15 and 17 respectively have pre-amplifiers 20 for converting the detected amount of laser beams into electrical signals, amplifying the signals and outputting them to lock-in amplifier 19.

According to the conventional laser spectroscopy system, the object gas to be measured is introduced in the reference cell 16 at a predetermined pressure, for example about 100 Torr and the sample gas flows through the sample cell 11 at a predetermined pressure, for example about 100 Torr. Under this condition, a laser beam of a predetermined wavelength is generated by the laser source 10 via the driving means 10a and 10b under the control of the control means 21, such as a personal computer. The amount of detected laser beams by the respective photo detectors 12, 15 and 17 are inputted to the control means 21 through the lock-in amplifier 19, and the amount of ingredients to be measured in the sample gas is acquired by calculations. The laser beam from the laser source 10 is irradiated as dispersion is removed by adjusting the diameter of the beam while passing the lens 22 or slit, pinhole or the like.

FIG. 4 is a diagram of an example of second derivative absorption spectra for measuring concentration of water molecules in hydrogen chloride by using the conventional laser spectroscopy system. The uppermost second derivative absorption spectrum X shows an absorption intensity of the laser beam detected by the first photo detector 12, wherein the laser beam is transmitted through the beam splitters 13 and 14 and the sample cell 11. The middle second derivative absorption spectrum Y shows an absorption intensity of the laser beam reflected by the beam splitter 13 and detected by the second photo detector 15. The lowermost second derivative absorption spectrum Z is acquired by subtracting the absorption intensity detected by the second photo detector 15 from the absorption intensity detected by the first photo detector 12, and is an absorption intensity of the water molecules in the sample gas flowing through the sample cell 11. According to what is described above, it is possible to cancel the absorption intensity of the beam other than that in the sample cell 11 line and to acquire only the absorption intensity of the water molecules in the sample gas in the sample cell 11 by subtracting the absorption intensity detected by the second photo detector 15 of the cancel line from the absorption intensity detected by the first photo detector 12 of the so called sample line. Therefore, it is possible to calculate the concentration of the water molecules in the hydrogen chloride by reading values of peak and valleys of the second derivative absorption spectrum Z.

In the real measurement, however, since it is rare to get such a clear second derivative absorption spectrum as shown in FIG. 4 and there is an undulation called "fringe noise" in the ordinary second derivative absorption spectrum, it is very difficult to measure a very small amount of ingredient with high precision. For example, FIG. 5 is a diagram of an example of second derivative absorption spectra of a refined and dehydrated hydrogen chloride flowing through the sample cell 11. As before, the lowermost second derivative absorption spectrum Z is acquired by subtracting the middle second derivative absorption spectrum Y from the uppermost second derivative absorption spectrum X. As shown in FIG. 5, though there is no water molecule in the sample gas, there is a large undulation by fringe noise in the second derivative absorption spectrum Z, so that there is a peak at the wavelength of water molecule's line.

This fringe noise is generated when the laser beam is transmitted or reflected through/by the inside wall and windows of the sample cell 11 and/or the beam splitters 13 and 14. When this fringe noise is generated, the measuring precision is deteriorated because a large distortion is generated in the valley area. For example, as shown in FIG. 6, if the fringe noise becomes larger, the peak P of water molecules, which originally would be represented as the upper spectrum of FIG. 6, is buried by the fringe noise Q, so that the measurement becomes difficult. Further, when other ingredient, such as carbon dioxide or hydrogen bromide in case of water molecule, of which the absorption wavelength is similar to that of the water molecule, exists, the peak R of the hydrogen bromide is located near the peak P of the water molecule, and it becomes difficult to distinguish the peaks and to perform precise measurement. These above described problems become much more serious particularly when a very small amount of impurities in a highly purified gas is analyzed.

Therefore, when analyzing water molecules, a 100% of water moisture is installed in the reference cell 16 with a prescribed pressure and the absorption wavelength of water molecule is identified by detecting the laser beam transmitted through the reference cell 16 by the third photo detector 17. In other words, even when the peak of the second derivative absorption spectrum Z is as small as the fringe noise, it is possible to clearly grasp the peak of absorption spectrum of the laser beam transmitted through the sample cell 11 by referencing the peak of the laser beam transmitted through the reference cell 16. As a result, it is possible to measure the amount of the water molecules with high precision. Further, by providing the reference cell 16 and the third photo detector 17, called reference line, even when the other ingredients of which the absorption wavelengths are similar exist, it is possible to clearly measure the only amount of water molecules.

However, because there is provided the reference cell 16 and the laser beam is splitted by the second beam splitter 14 on the beam path, the power of the laser source 10 should be sufficiently large and this causes not only cost up but also larger fringe noise.

Further, as shown in FIG. 8, a focusing lens 23 is provided at the rear of the laser source 10 in order to converge the rear dispersion of the laser source 10, and the converged laser beam is irradiated to the reference cell 16 and detected by the third photo detector 17. In this case, however, since additional elements are provided on the axis of laser beam, the whole system becomes larger and more space is required.

In case the optical system is contained in a purge box 18, the volume of the purge box 18 should be increased due to installment of the reference cell 16. In order to change the atmosphere in the purge box 18, for example from the air to nitrogen atmosphere with water adjustment, the purging efficiency is decreased and the required time for purging is increased. Therefore, the system setup time becomes longer and the consumption of nitrogen gas is increased.

Because the reference cell 16 is provided, it is needed to add the beam splitter 14 and the focusing lens 23, and the number of required elements is drastically increased and the manufacturing cost is also increased.

SUMMARY OF THE INVENTION

Therefore, it is an object of the present invention to provide a laser spectroscopy system of simple construction and free of the influence of the fringe noise.

It is another object of the present invention to provide a laser spectroscopy system in which a reference cell is efficiently installed with minimum cost and space.

In accordance with an aspect of the present invention, there is disclosed a laser spectroscopy system including: a tunable laser diode source for generating a laser beam used for spectroscopic analysis; a sample cell where a sample gas is introduced; a first photo detector for measuring an intensity of a laser beam transmitted through the sample cell and having a beam receiving face; a beam splitter for splitting a portion of the laser beam from the laser source; and a second photo detector for measuring an intensity of a splitted laser beam from the beam splitter and having a beam receiving face, wherein the at least one of beam receiving faces is tilted to be at a predetermined angle from an axis of laser beam.

Further, the laser spectroscopy system according to the present invention further includes a reference cell, where an object to be measured is introduced, being positioned on a beam path of a laser beam reflected from the beam receiving face of the at least one of the photo detector of which the beam receiving face is tilted; and a third photo detector for measuring an intensity of a laser beam transmitted through the reference cell.

BRIEF DESCRIPTION OF THE DRAWINGS

A further understanding of the nature and advantage of the present invention will become apparent by reference to the remaining portions of the specification and drawings.

DETAILED DESCRIPTION OF THE PREFERRED EMBODIMENT

Figure 1:
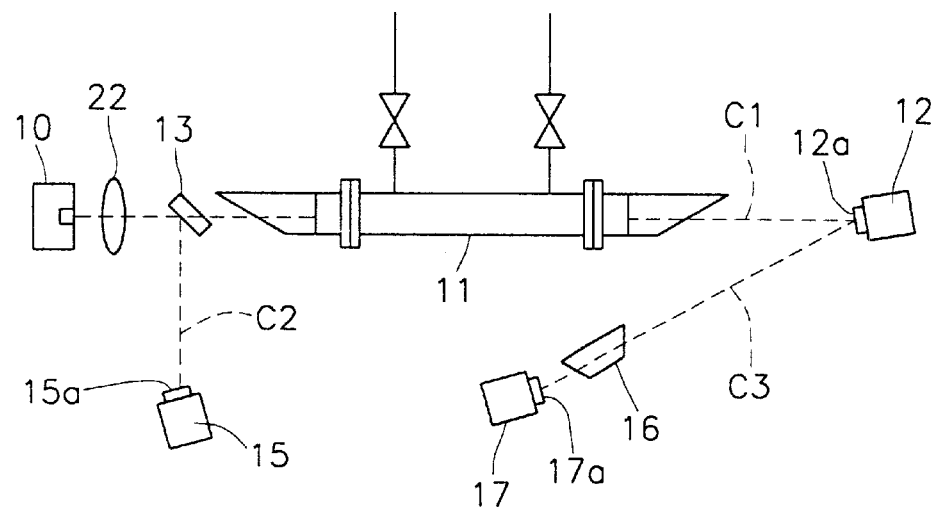
FIG. 1 is a schematic diagram which shows a configuration of an embodiment of a laser spectroscopy system according to the present invention.
Figure 3:
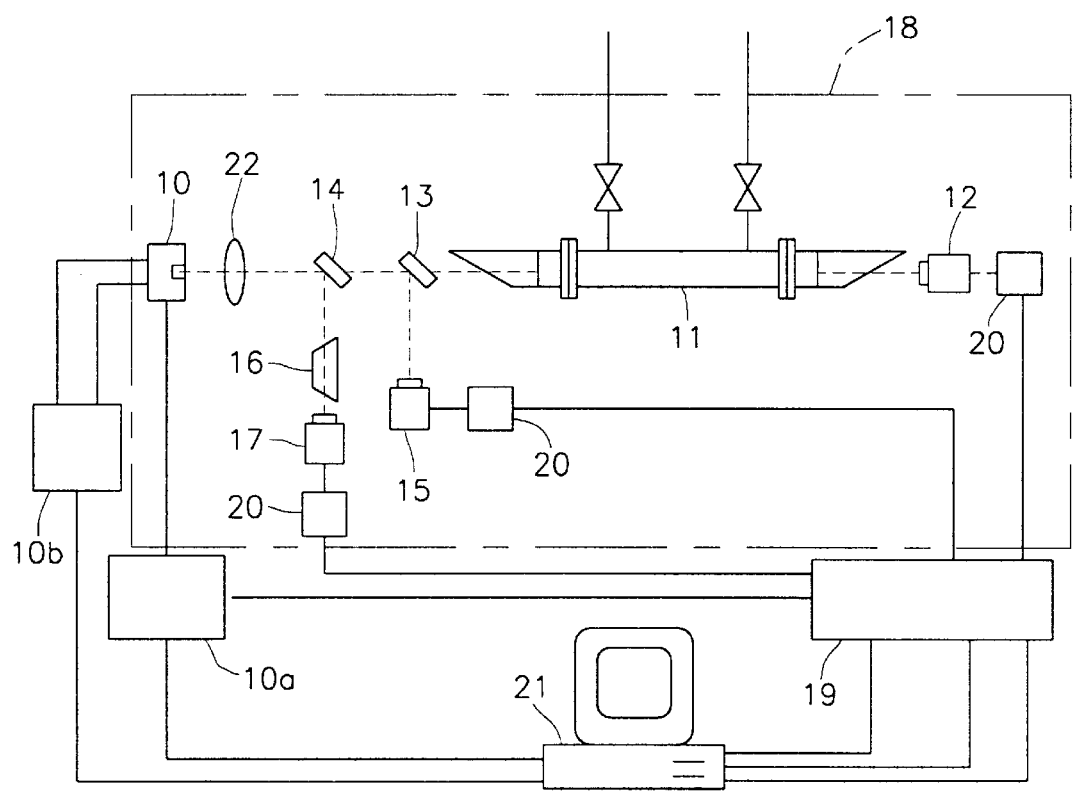
FIG. 3 is a diagram which shows an example of the conventional laser spectroscopy system.
Figure 4:
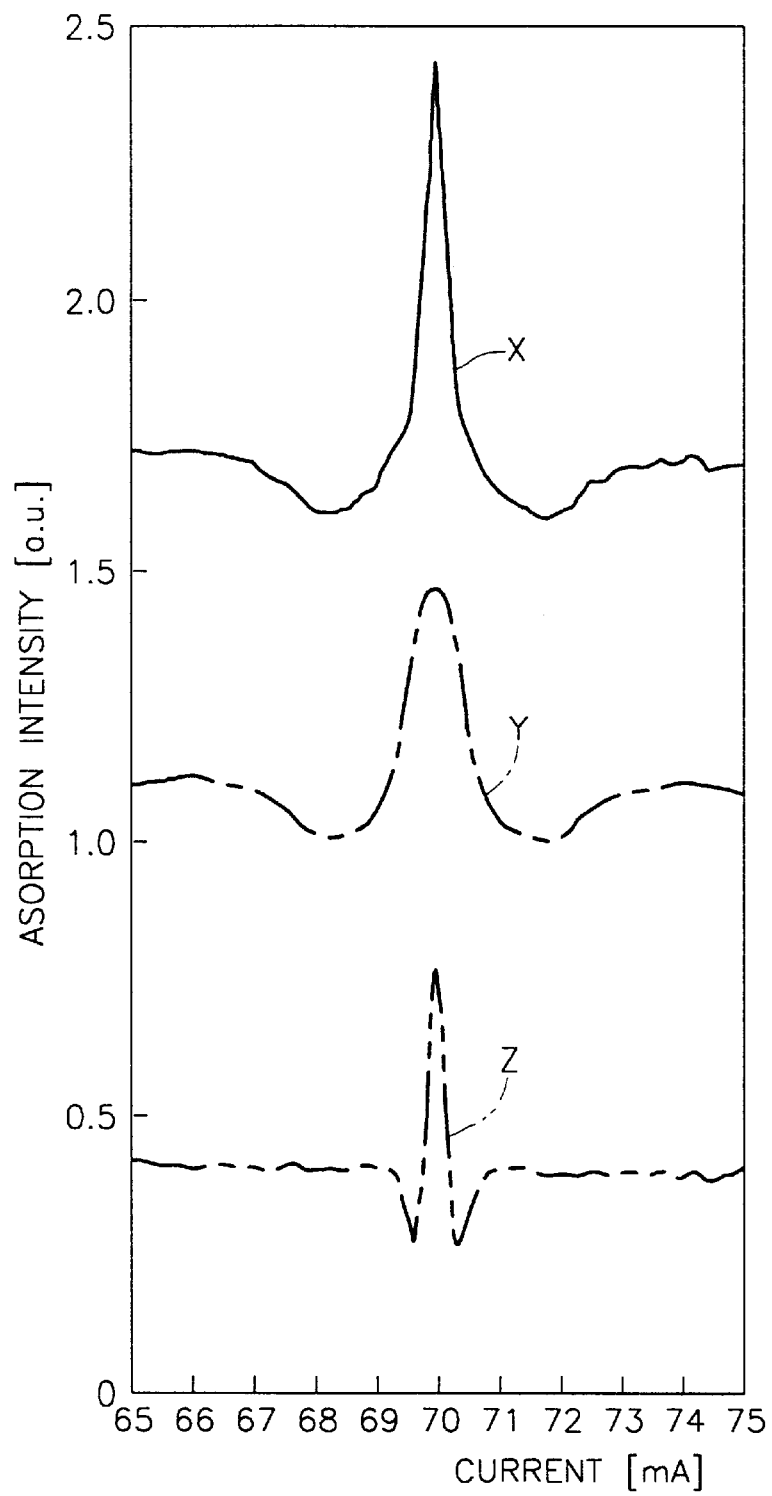
FIG. 4 is a diagram of an example of second derivative absorption spectra for measuring the concentration of water molecules in hydrogen chloride.
Figure 5:
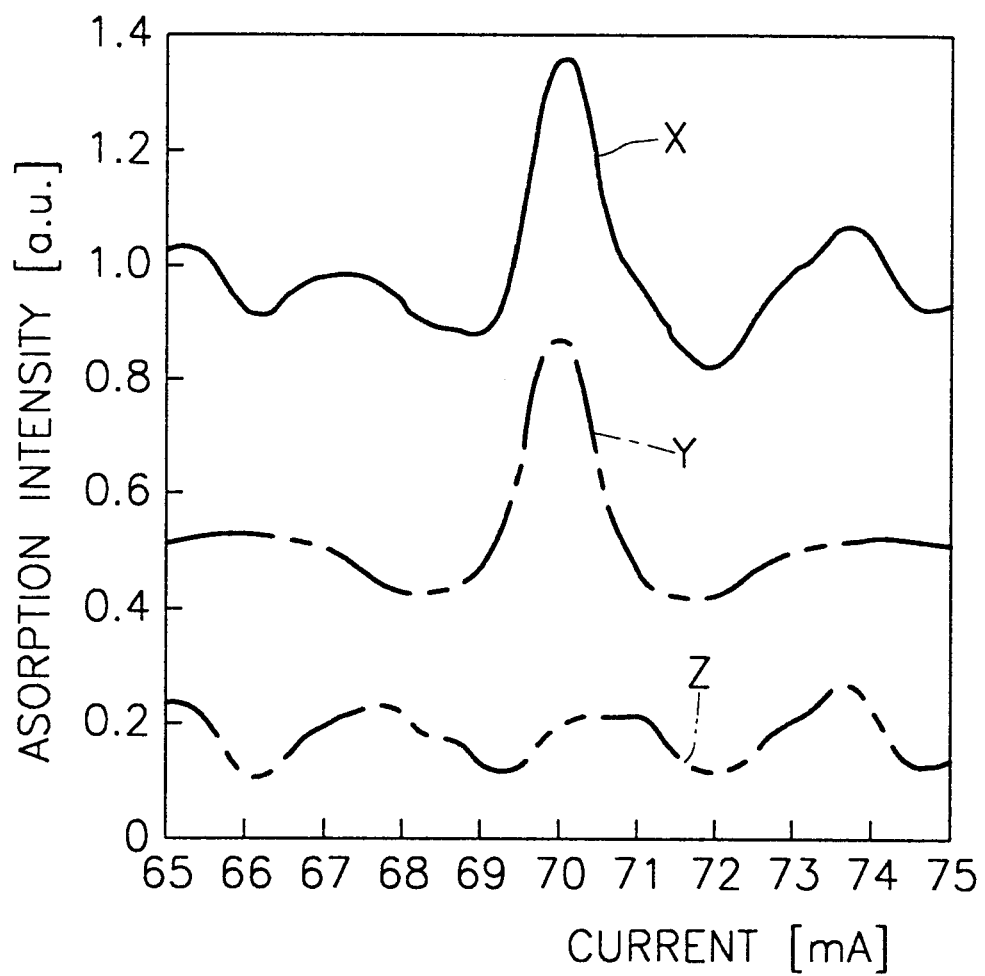
FIG. 5 is a diagram which shows a state where a fringe noise is generated in the absorption spectrum.
Figure 6:
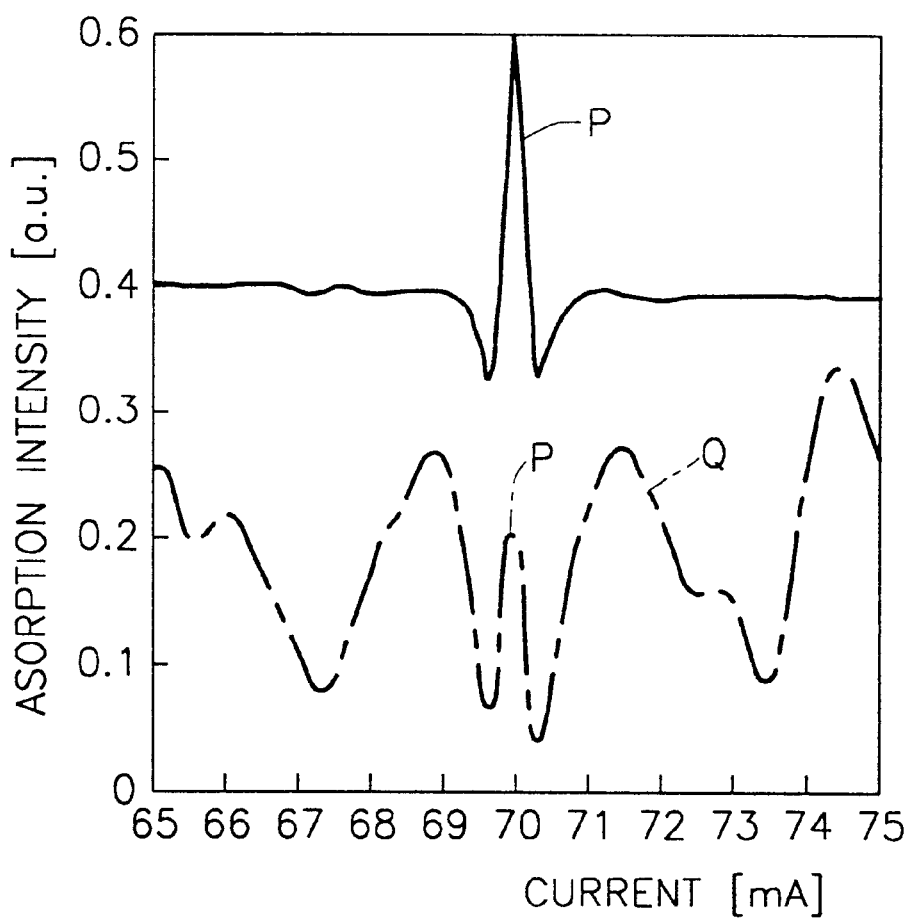
FIG. 6 is a diagram which shows a state where a measurement peak is buried by the fringe noise.
Figure 7:
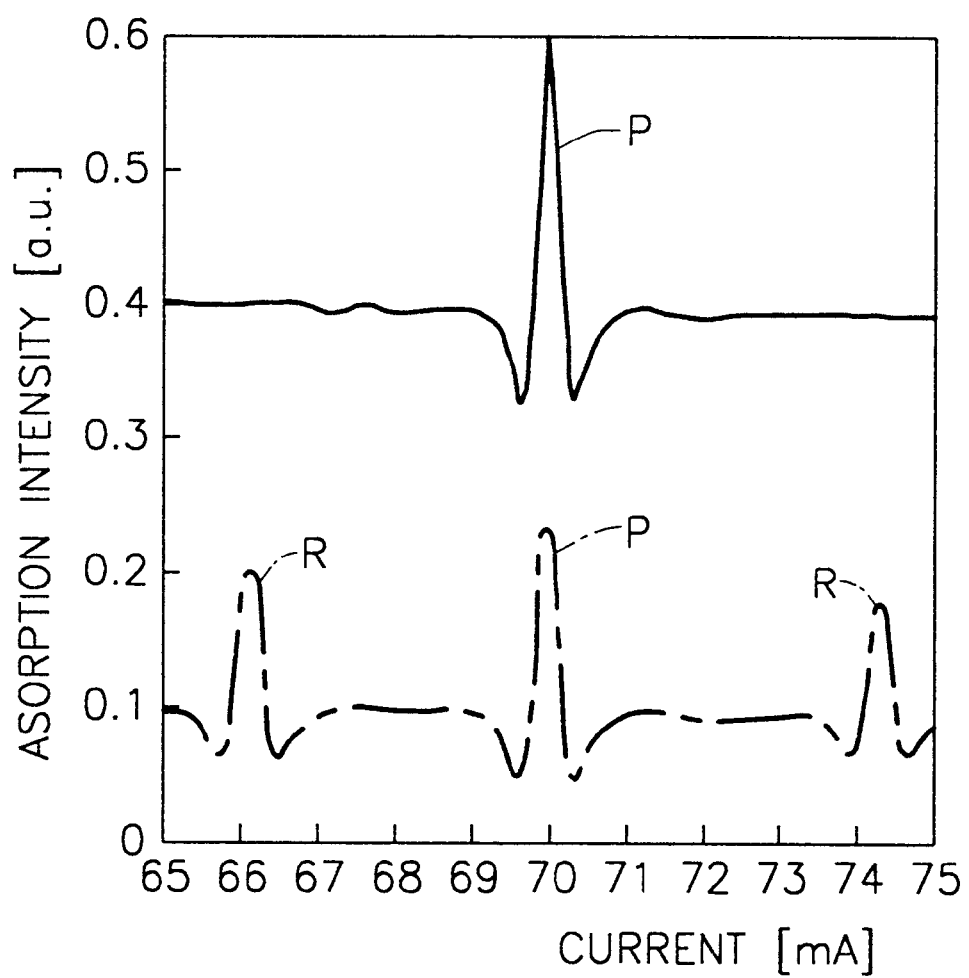
FIG. 7 is a diagram which shows a state where peaks of other ingredients, of which the absorption wavelengths are similar, appear.
Figure 8:
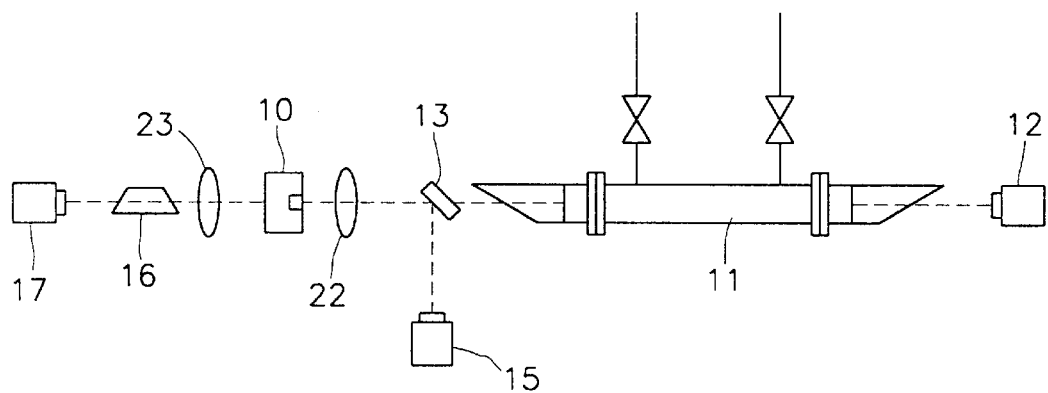
FIG. 8 is a schematic diagram of an optical system which shows a configuration of other embodiment of a reference cell of the conventional laser spectroscopy system.

FIG. 1 is a schematic diagram which shows a configuration of an embodiment of a laser spectroscopy system according to the present invention. Hereinafter, the same elements shown in FIG. 1 as those shown in FIG. 3 are designated by the same reference numbers, and the detailed description of those elements are omitted. Since other portions than the optical system can be embodied similarly to those of conventional spectroscopy system, the detailed description of them is also omitted.

The laser spectroscopy system of the present invention includes a tunable laser diode source 10, a sample cell 11 and a first photo detector 12 forming a sample line, and a beam splitter 13 and a second photo detector 15 forming a cancel line. They are organized as in the conventional spectroscopy system, so that a concentration of a very small amount of ingredient (object to be measured) in a gas is measured by acquiring a second derivative absorption spectrum from the beam intensities detected by the first and the second photo detectors 12 and 15 as in the case of conventional spectroscopy system.

In the spectroscopy system shown in FIG. 1, beam receiving faces 12a and 15a of the photo detectors 12 and 15 are tilted to be at a predetermined angle from the axes C1 and C2 of laser beam. If the beam receiving faces 12a and 15a are perpendicular to the axes of laser beam (also referred to as "beam axes") as in the conventional spectroscopy system, the laser beams incident to the detectors 12 and 15 are reflected by the receiving faces 12a and 15a to the beam axes C1 and C2 and propagated in the reverse direction of the beam path. The reflected beams returning to the detectors 12 and 15 become the source of the fringe noises due to the difference of beam paths length. Therefore, it is possible to reflect the beams at the receiving faces 12a and 15a to the other ways than the beam axes C1 or C2, and to prevent fringe noises due to the double reflection from occurring by tilting the receiving faces 12a and 15a at a predetermined angle, preferably in the range of about 10 to 30 degrees or more preferably at an angle of about 15 degree, from the axes C1 or C2, respectively. If the tilting angle is small, it is probable for the reflected beams to return on the direction of beam path to cause the fringe noises. On the other hand, if the tilting angle is too large, it becomes difficult to control the beam axes because effective beam receiving area becomes too small.

On the beam path of the reflected laser beam by the tilted beam receiving face 12a of the first photo detector 12, a reference line is provided to include a reference cell 16, where an object to be measured is introduced under depressurized condition, and a third photo detector 17 for measuring the intensity of laser beam transmitted through the reference cell 16. As in the conventional spectroscopy system, the reference cell 16 and the third photo detector 17 are used for clearly identifying the absorption wavelength of the object to be measured, and by providing them, it is possible to measure the object to be measured with high precision and high sensitivity while decreasing the influence of fringe noises or other ingredients of which the absorption wavelengths are similar. Further, as for the third photo detector 17 also, it is possible to prevent a fringe noise from being generated by the reflected beam at beam receiving face 17a by tilting the beam receiving face 17a of the third photo detector 17 at a predetermined angle from the beam axis C3.

Therefore, the sensitivity and precision of measurement of object to be measured are greatly increased by decreasing the fringe noises through tilting the beam receiving faces 12a, 15a and 17a of the photo detectors 12, 15 and 17 from the beam axes C1, C2 and C3 and by clearly identifying the absorption wavelength through providing the reference cell 16.

By providing reference cell 16 and the third photo detector 17 on the beam path of the laser beam reflected at the beam receiving face 12a of the photo detector 12, it is not needed to increase output power of the laser source 10 and to add elements, such as the beam splitter or focusing lens, and it is possible to make the length of the optical system in the direction of beam axis as that of the conventional spectroscopy system which does not have the reference cell. Further, since it is possible to decrease the number of elements and to reduce the size of the system, it becomes possible to reduce the manufacturing cost. Since it is possible to miniaturize the purge box covering the optical system by miniaturizing the optical system as described above, it is possible to shorten the required time for purging the purge box with nitrogen gas or other gas, to rapidly set up the system and to reduce the consumption of nitrogen gas or other gas.

In case a gas including solidification ingredients, for example an exhausted gas from CVD (Chemical Vapor Deposition) apparatus, is flowed through the sample cell 11, the solidification ingredients stick on the windows of the sample cell 11 and causes the amount of transmitted beams to be decreased, so that it is required to clean or change the windows. In this case, as described above, if the system is formed as the laser beam transmitted through the sample cell 11 and reflected at the first photo detector 12 is incident to the third photo detector 17 through reference cell 16, it is possible to know the decrease in the amount of beam transmitted through the sample cell 11 from the decrease in the intensity of receiving beam at the third photo detector 17, so that it is possible to know the time for cleaning or changing the windows of the sample cell 11.

Figure 2:
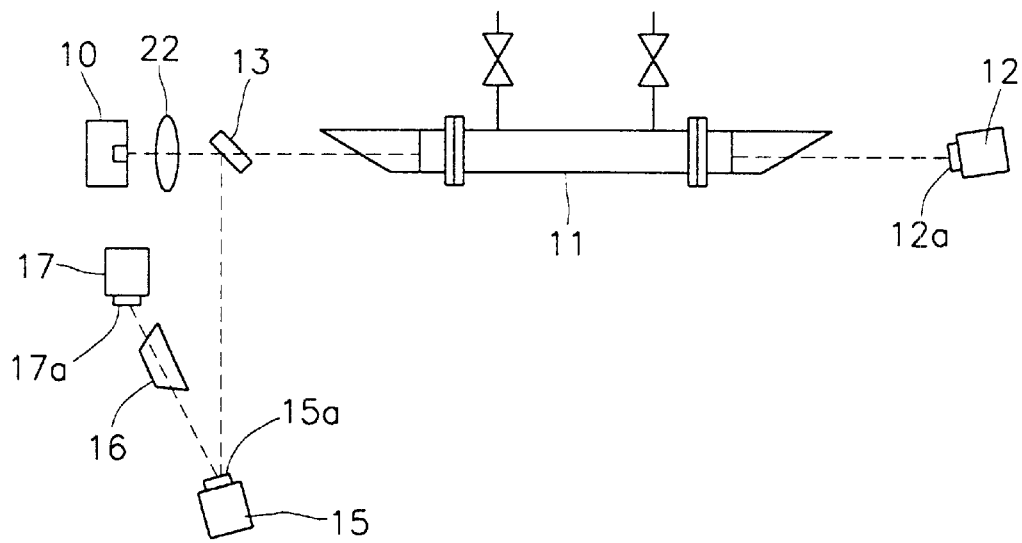
FIG. 2 is a diagram of an optical system which shows a configuration of another embodiment of a reference cell of a laser spectroscopy system according to the present invention.

As shown in FIG. 2, the reference cell 16 and the third photo detector 17 may be provided on the beam path of the laser beam reflected at the second photo detector 15. Further, it is not necessary to tilt all of the beam receiving faces 12a, 15a and 17a, and enough to tilt the only beam receiving face which causes the reflected beam to be incident to the reference cell 16 and the third photo detector 17.

As described above, according to the laser spectroscopy system of the present invention, it is possible to increase the measurement precision by reducing the fringe noise and to provide the reference cell at low cost.

Although the preferred embodiment of the present invention has been disclosed for illustrative purposes, those skilled in the art will appreciate that various modifications, additions and substitutions are possible, without departing from the scope and the spirit of the present invention as disclosed in the accompanying claims.

What is claimed is:

1. A laser spectroscopy system comprising:
   a tunable laser diode source for generating a laser beam used for spectroscopic analysis;
   a sample cell where a sample gas is introduced;
   a first photo detector for measuring an intensity of a laser beam transmitted through said sample cell and having a beam receiving face;
   a beam splitter for splitting a portion of said laser beam from said laser source; and
   a second photo detector for measuring an intensity of a splitted laser beam from said beam splitter and having a beam receiving face,
   wherein said at least one of beam receiving faces is tilted to be at a predetermined angle from an axis of laser beam.

2. A laser spectroscopy system as claimed in claim 1 further comprising:
   a reference cell, where an object to be measured is introduced, being positioned on a beam path of a laser beam reflected from said beam receiving face of said at least one of said photo detector of which said beam receiving face is tilted; and
   a third photo detector for measuring an intensity of a laser beam transmitted through said reference cell.

* * * * *